US00PP18399P3

(12) United States Plant Patent
Pierce

(10) Patent No.: US PP18,399 P3
(45) Date of Patent: Jan. 1, 2008

(54) ***CALIBRACHOA* PLANT NAMED 'CAL BULROSE'**

(50) Latin Name: ***Calibrachoa* sp.**
Varietal Denomination: Cal Bulrose

(75) Inventor: Robert Osteen Pierce, Watsonville, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 59 days.

(21) Appl. No.: 11/352,968

(22) Filed: Feb. 13, 2006

(65) Prior Publication Data

US 2007/0192917 P1 Aug. 16, 2007

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—S. B. McCormick-Ewoldt
(74) *Attorney, Agent, or Firm*—Jondle & Associates, P.C.

(57) ABSTRACT

A new *Calibrachoa* plant particularly distinguished by medium to large red-purple flowers, early and continuous flowering, medium green foliage with narrow, elliptical leaves, and a semi-vigorous, medium tight plant habit with good branching ability and a spreading to prostrate and later trailing habit, is disclosed.

2 Drawing Sheets

Genus and species: *Calibrachoa* sp.
Variety denomination:
'Cal Bulrose'.

BACKGROUND OF THE NEW PLANT

The present invention comprises a new and distinct cultivar of *Calibrachoa,* botanically known as *Calibrachoa* sp., and hereinafter referred to by the cultivar name 'Cal Bulrose'. The new cultivar originated from a hybridization made in July 2002 in Gilroy, Calif. The female parent was the proprietary blue-flowered *Calibrachoa* plant '672-1' (unpatented), while the male parent was the proprietary *Calibrachoa* plant '646-1' (unpatented) having light-red variegated flowers. The seeds produced by the hybridization were sown in January 2003 in Gilroy, Calif. A single plant selection was chosen for further evaluation and for asexual propagation in summer 2003 in Gilroy, Calif.

The new cultivar was created in 2002 in Gilroy, Calif. and has been asexually reproduced repeatedly by vegetative cuttings and tissue culture in Gilroy, Calif. over a two-year period. 'Cal Bulrose' has not been observed under all possible environmental conditions. The present invention has been found to retain its distinctive characteristics through successive asexual propagations.

Plant Breeder's Rights for this cultivar were applied for in Canada on Mar. 29, 2005, in Switzerland on Sep. 16, 2005 and with the European Union on Sep. 28, 2005.

SUMMARY OF THE INVENTION

The following are the most outstanding and distinguishing characteristics of this new cultivar when grown under normal horticultural practices in Gilroy, Calif. and Hillscheid, Germany.

1. Medium to large, red-purple flowers;
2. Medium-green foliage with narrow, elliptical leaves;
3. Medium size, semi-vigorous, tight plant habit;

4. A spreading to prostrate and later trailing habit;
5. Good branching ability; and
6. An early and continuous flowering response.

DESCRIPTION OF PHOTOGRAPHS

This new *Calibrachoa* plant is illustrated by the accompanying photographs which show overall plant habit including blooms, buds, and foliage of the plant; the colors shown are as true as can be reasonably obtained by conventional photographic procedures. The photographs are of a whole plant about 11-weeks old, grown in a greenhouse in Hillscheid, Germany, in May of 2005.

DESCRIPTION OF THE NEW CULTIVAR

Figure 1:
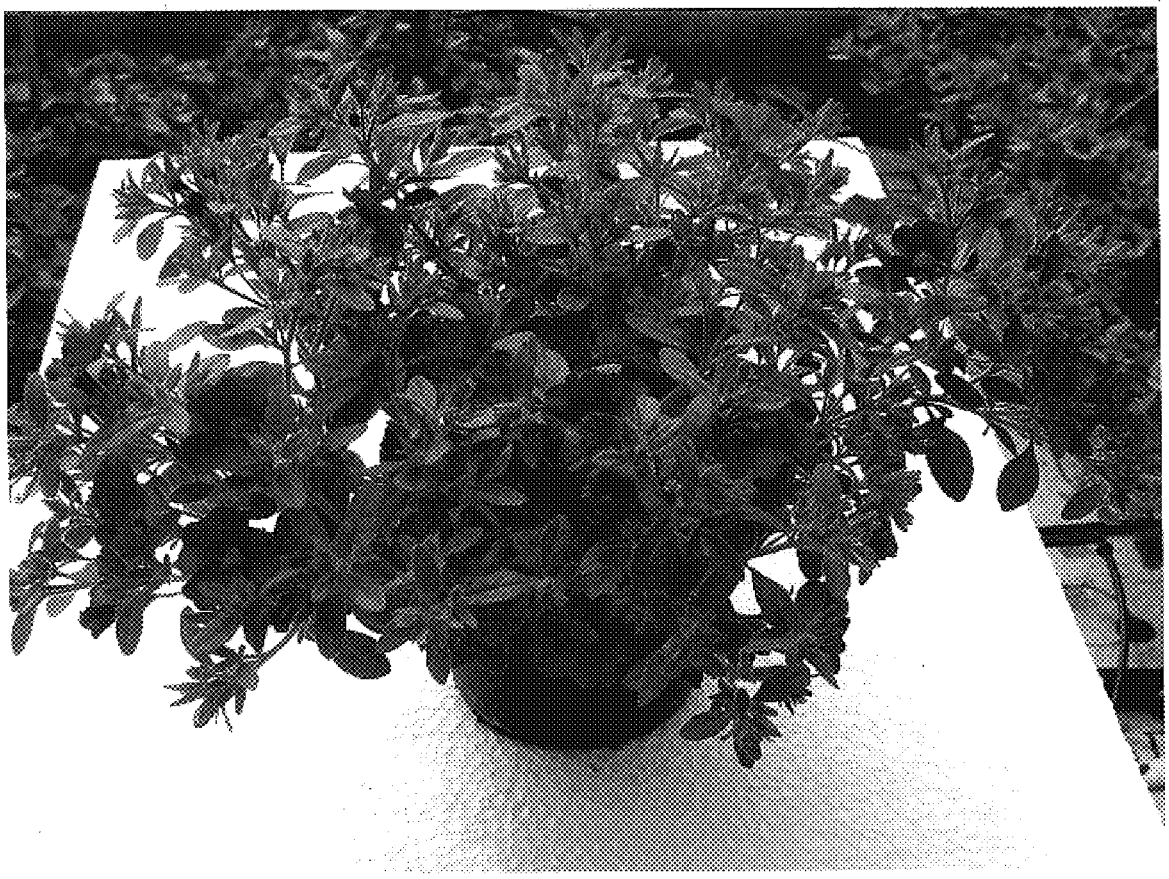
FIG. 1 shows the overall plant habit, including blooms, buds and foliage.
Figure 2:
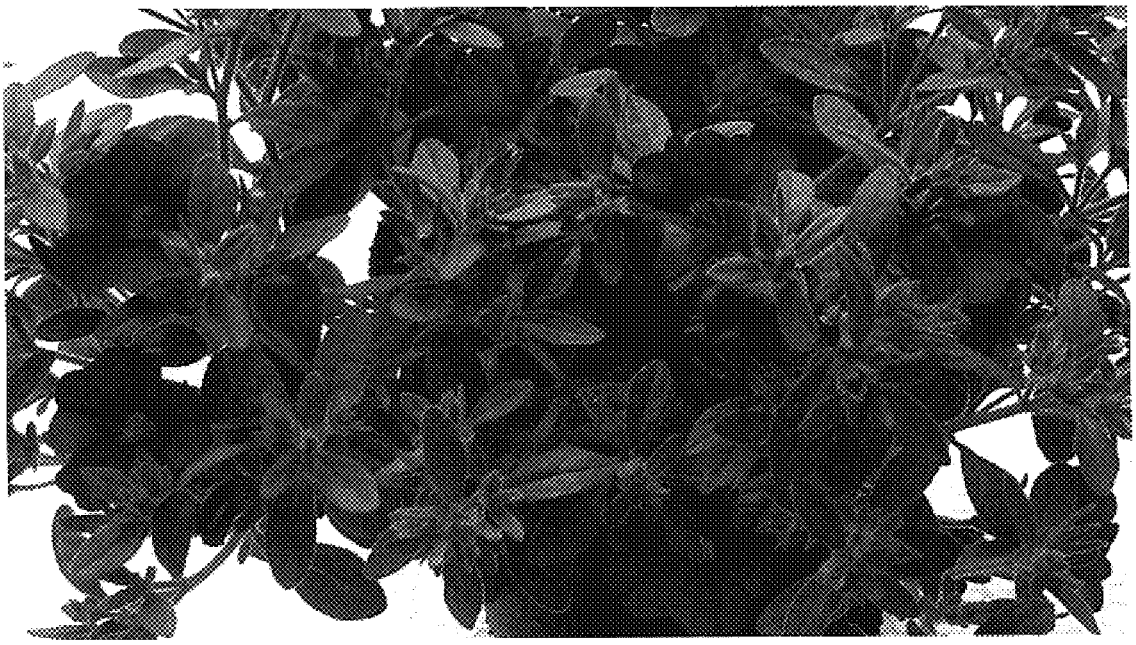
FIG. 2 shows a close-up of the mature inflorescences.

The following detailed description sets forth the distinctive characteristics of 'Cal Bulrose'. The data which define these characteristics were collected from asexual reproductions carried out in Hillscheid, Germany. The plant history was taken on 7-week old unpinched plants which were planted as rooted cuttings in 12-cm pots in early July 2005, and then grown in a greenhouse. Observations were made when the plants were in full flower in August 2005. Color readings were taken under natural light in the greenhouse. Color references are primarily to the R.H.S. Colour Chart of The Royal Horticultural Society of London (R.H.S.) (2001).

DETAILED BOTANICAL DESCRIPTION OF THE NEW PLANT

Classification:
*Family.*—Solanaceae.
*Botanical.*—*Calibrachoa* sp.
*Common name.*—*Calibrachoa.*

Parentage:

*Female parent.*—'672-1' a proprietary blue-flowered *Calibrachoa* plant (unpatented).

*Male parent.*—'646-1', a proprietary light-red variegated-flowered *Calibrachoa* plant (unpatented).

Growth:

*Form.*—Herbaceous perennial, usually cultivated as an annual plant.

*Habit.*—Spreading low or decumbent, free branching (high number of branches), moderately compact.

*Height* (*measured from the top of the soil*).—17.5 cm.

*Width* (*horizontal plant diameter*).—35 cm.

*Propagation.*—Terminal tips for cuttings.

*Time to produce a finished lowering plant.*—9 to 10 weeks for a 12-cm pot.

*Outdoor plant performance.*—For hanging baskets and containers.

*Time to initiate and develop roots.*—About 24 days.

*Root description.*—Fibrous.

Stems:

*Average number* (*basal plus secondary*).—31.0.

*Length of basal branches (from the base of the stem to the tip): 20 cm.*

*Internode length.*—1.0 cm to 1.5 cm.

*Diameter of branches* (*from midpoint*).—0.2 cm to 0.25 cm.

*Stem color.*—Mainly RHS 146C due to very weak infusion of anthocyanin; RHS 143B (green) for young branches.

*Texture.*—Somewhat rough with short coarse hair.

Leaves:

*Arrangement.*—Initially alternate, later appear mostly opposite with flowering branches.

*Size.*—Length: 2.8 cm. Width: 1.1 cm.

*Shape.*—Lanceolate to narrowly elliptic.

*Margin.*—Entire.

*Apex.*—Obtuse to rounded.

*Base.*—Attenuate.

*Color* (*mature leaves*).—Upper surface: RHS 137B to RHS 137C. Lower surface: RHS 138A to RHS 138B.

*Texture.*—Velvety with fine pubescence.

*Venation.*—Pinnate (indistinct).

*Venation color.*—RHS 145B (pale light-green) for the midrib of the lower surface.

*Variegation.*—None.

*Petioles.*—Length: 0.3 cm to 0.5 cm (not clearly distinct from the base of the leaf). Width: 0.1 cm to 0.2 cm. Color: RHS 145A. Texture: Covered with pubescence.

Flower bud:

*Shape.*—Tube-shaped to narrow funnel-shaped.

*Size.*—Length: 2.2 cm. Diameter: 0.5 cm to 0.6 cm.

*Color at tight bud.*—Mainly RHS 162B (ochre-yellow).

Inflorescence:

*Blooming habit.*—Continuous from Spring to Fall.

*Inflorescence type.*—Flowers appear solitary, emerging from the leaf axil.

*Floret type.*—Base is funnel-shape with fused petals; lobes are directed outward and salver-shaped.

*Number of flowers per node.*—1.

*Lastingness of individual blooms on the plant.*—6 days.

*Size.*—Width (flower face): 3.3 cm. Length (flower face): 3.1 cm. Depth (total length of flower): 2.3 cm. Funnel: Length (from below): 1.9 cm. Diameter (at opening): Up to 1.1 cm.

*Fragrance.*—Weak, petunia-like.

*Peduncle.*—Color: RHS 143C (light-green). Length: 2.0 cm. Diameter: 0.1 cm. Texture: Covered with dense pubescence.

Flowers:

*Immature flower.*—Diameter: About 2.5 cm. Color: Near RHS N74A (intense red-purple), occasionally RHS N66A, often with RHS 79B (dark purple) ring around the funnel.

*Mature flower color* (*front view of petal lobes*).—RHS N74B; some tend to fade to RHS 67B, the violet ring in the immature flower usually fades and disappears as the flowers matures.

*Corolla.*—Shape of corolla: Tube-shaped. Color inside: RHS 12A (brilliant yellow). Color outside: RHS 162D, with fine dark veins. Outside texture: Somewhat rippled lengthwise.

*Petals.*—Shape: Lower part is fused and upper part is lobe free. Apex: Mostly truncate, very weakly emarginate. Base: Fused. Margin: Entire. Waviness of petals: Very weak. Lobation: Weak. Texture: Smooth.

*Sepals.*—Shape: Ensiform. Apex: Obtuse. Base: Fused. Margin: Entire. Length: 1.0 cm. Width: 0.3 cm. Color RHS 143 (green). Texture: Dense pubescence. Pubescence color: Whitish.

Reproductive organs:

*Stamens.*—Number: 5 (various lengths). Filament color: RHS 155A (whitish). Filament length: 0.9 cm to 1.3 cm. Filament diameter: 0.1 cm. Pollen color: RHS 6D (pale-yellow). Pollen quantity: Moderate.

*Pistil.*—Number: 1. Length: 1.1 cm. Diameter 0.1 cm. Stigma color: RHS 145A (light-green). Style color: RHS 145C.

Fruit and seed set: No seed set observed.

Disease and insect resistance: No particular resistance or susceptibility has been observed.

COMPARISON WITH PARENTAL AND COMMERCIAL CULTIVARS

'Cal Bulrose' differs from the female parent '672-1' (unpatented), by having red-purple flowers, while '672-1' has blue flowers. In addition, 'Cal Bulrose' has larger leaves than '672-1'.

'Cal Bulrose' differs from the male parent '646-1' (unpatented), by having red-purple flowers while '646-1' has light-red flowers. In addition, 'Cal Bulrose' has a more prostrate plant habit with stronger basal branching than '646-1'.

'Cal Bulrose' differs from the commercial cultivar 'Cal Rose' (U.S. Plant Pat. No. 14,606), by having larger flowers that are lighter red-purple with a less distinct dark ring around the flower opening than 'Cal Rose'. Additionally, 'Cal Bulrose' has wider leaves and a denser plant with stronger branching than 'Cal Rose'.

I claim:

1. A new and distinct cultivar of *Calibrachoa* plant as shown and described herein.

* * * * *